US009138255B2

(12) United States Patent
Oostman et al.

(10) Patent No.: US 9,138,255 B2
(45) Date of Patent: Sep. 22, 2015

(54) ANTI-POPPING DEVICES AND METHODS FOR HAIR IMPLANTATION

(75) Inventors: Clifford A. Oostman, Hansville, WA (US); Robert L. Weglinski, Oakland, CA (US); Timothy J. Kirkley, Sunnyvale, CA (US)

(73) Assignee: Restoration Robotics, Inc., San Jose, CA (US)

( * ) Notice: Subject to any disclaimer, the term of this patent is extended or adjusted under 35 U.S.C. 154(b) by 113 days.

(21) Appl. No.: 13/545,807

(22) Filed: Jul. 10, 2012

(65) Prior Publication Data

US 2012/0310267 A1 Dec. 6, 2012

Related U.S. Application Data

(62) Division of application No. 12/683,155, filed on Jan. 6, 2010, now Pat. No. 8,241,314.

(60) Provisional application No. 61/145,088, filed on Jan. 15, 2009.

(51) Int. Cl.
*A61B 17/34* (2006.01)
*A61B 17/3205* (2006.01)
*A61B 17/00* (2006.01)

(52) U.S. Cl.
CPC ....... *A61B 17/3468* (2013.01); *A61B 17/32053* (2013.01); *A61B 2017/00752* (2013.01)

(58) Field of Classification Search
CPC ................. A61B 17/32053; A61B 17/3468; A61B 17/34; A61B 2017/00752
USPC .......... 606/187, 213, 133, 184, 167, 185, 172
See application file for complete search history.

(56) References Cited

U.S. PATENT DOCUMENTS 3,596,292 A * 8/1971 Erb et al. .................... 623/15.11
3,699,969 A 10/1972 Allen
(Continued)

FOREIGN PATENT DOCUMENTS

WO 97-06749 2/1997
WO 2009017445 2/2009

OTHER PUBLICATIONS

Inaba M. and Inaba, Y. "Androgenetic Alopecia, Modern Concepts of Pathogenesis and Treatment, 29. Operative Treatment for Androgenetic Alopecia." Springer, pp. 238-244, 309. 1996.
(Continued)

*Primary Examiner* — Tuan V Nguyen
*Assistant Examiner* — Tin Nguyen
(74) *Attorney, Agent, or Firm* — Lena I. Vinitskaya; Sharon Upham (57) ABSTRACT

A system and method for implanting follicular units (FUs) into a body surface while suppressing expulsion of previously-implanted FUs. The system is particularly useful to facilitate hair transplant procedures. FUs are implanted in a body surface from an implant tool or needle that may be incorporated within an automated or robotic system, or may form part of a semi-automated or even manual apparatus. An anti-popping member prevents expulsion of the FUs adjacent to the location at which an FU is being implanted. The anti-popping member may be carried on the implant device, or may be a flexible membrane applied to the body surface. If on the device, the anti-popping member may be arranged near the distal tip thereof and may be shaped and mounted so as to conform to uneven body surfaces.

22 Claims, 3 Drawing Sheets

(56) References Cited

U.S. PATENT DOCUMENTS

| | | | |
|---|---|---|---|
| 4,004,592 | A | 1/1977 | Yamada |
| 4,451,254 | A | 5/1984 | Dinius et al. |
| 4,579,120 | A | 4/1986 | MacGregor |
| 4,755,173 | A | 7/1988 | Konopka et al. |
| 5,215,531 | A | 6/1993 | Maxson et al. |
| 5,267,968 | A | 12/1993 | Russo |
| 5,354,283 | A | 10/1994 | Bark et al. |
| 5,484,420 | A | 1/1996 | Russo |
| 5,584,841 | A | 12/1996 | Rassman |
| 5,658,272 | A * | 8/1997 | Hasson .......................... 606/1 |
| 5,782,851 | A | 7/1998 | Rassman |
| 5,817,120 | A | 10/1998 | Rassman |
| 5,951,572 | A | 9/1999 | Markman |
| 6,059,807 | A | 5/2000 | Boudjema |
| 6,120,521 | A | 9/2000 | Casparian |
| 6,585,746 | B2 | 7/2003 | Gildenberg |
| 7,008,402 | B2 | 3/2006 | Ferguson et al. |
| 7,452,367 | B2 | 11/2008 | Rassman |
| 7,691,089 | B2 | 4/2010 | Gresham |
| 7,785,339 | B2 * | 8/2010 | Cohen ........................... 606/187 |
| RE42,437 | E | 6/2011 | Gildenberg |
| 7,981,120 | B2 | 7/2011 | Mazzocchi et al. |
| 7,999,145 | B2 | 8/2011 | Kairinos |
| 2004/0092924 | A1 | 5/2004 | Vasa |
| 2004/0116894 | A1 | 6/2004 | DeLegge |
| 2004/0267284 | A1 * | 12/2004 | Parmer et al. ................. 606/130 |
| 2005/0070920 | A1 | 3/2005 | Solar et al. |
| 2005/0085795 | A1 | 4/2005 | Lockwood et al. |
| 2005/0096687 | A1 | 5/2005 | Rassman et al. |
| 2005/0267415 | A1 | 12/2005 | Jacques |
| 2006/0135950 | A1 | 6/2006 | Gomez |
| 2006/0293703 | A1 | 12/2006 | Pak et al. |
| 2007/0038100 | A1 | 2/2007 | Nita |
| 2007/0078475 | A1 * | 4/2007 | Bodduluri et al. ............ 606/187 |
| 2007/0106217 | A1 | 5/2007 | DeLegge et al. |
| 2007/0106306 | A1 | 5/2007 | Bodduluri et al. |
| 2008/0009896 | A1 | 1/2008 | Shiao |
| 2008/0051816 | A1 | 2/2008 | Pak et al. |
| 2008/0082081 | A1 | 4/2008 | Melsheimer |
| 2008/0234697 | A1 | 9/2008 | DuBois |

OTHER PUBLICATIONS

Robert M. Bernstein; William R. Rassman; Wojciech Szaniawski; Alan J. Halperin. "Follicular Transplantation". International Journal of Aesthetic and Restorative Surgery. vol. 3, No. 2, 1995, pp. 119-132. 1995.

Robert M. Bernstein; William R. Rassman. "The Logic of Follicular Unit Transplantation". Dermatologic Clinics vol. 17, No. 2, Apr. 1999.

William R. Rassman, MD; Robert M. Bernstein, MD. "Rapid Fire Hair Implanter Carousel". Dermatologic Surgery, vol. 24, 1998, pp. 623-627.

Dong-Youn Lee, Joo-Heung Lee, Jun-Mo Yang, Eil-Soo Lee. "New Instrument for Hair Transplant: Multichannel Hair Transplanter", Dermatol Surg 2005, 31: 379. Published by BC Decker Inc.

* cited by examiner

ANTI-POPPING DEVICES AND METHODS FOR HAIR IMPLANTATION

RELATED APPLICATIONS

The present application is a division of U.S. patent application Ser. No. 12/683,155 filed Jan. 6, 2010 now U.S. Pat. No. 8,241,314 and entitled "Anti-popping Devices and Methods for Hair Implantation," which claims priority under 35 U.S.C. 119(e) to U.S. Provisional Application No. 61/145,088 filed Jan. 15, 2009, entitled "Anti-Popping Devices and Methods for Hair Implantation." These applications are each hereby incorporated by reference in their entirety.

FIELD OF THE INVENTION

The invention relates generally to devices, systems and methods for implanting follicular units in a body surface and, in particular, for implanting hair grafts or hair follicles in a hair transplantation procedure.

BACKGROUND OF THE INVENTION

Hair transplantation procedures are well-known, and typically involve harvesting donor hair grafts from the "donor areas," for example, side and back fringe areas of the patient's scalp, and implanting them in a bald area ("recipient area"). Historically, the harvested hair grafts were relatively large (3-5 mm), although more recently the donor grafts may be single "follicular units" (FUs) which are naturally occurring aggregates of 1-3 (and much less commonly, 4-5) closely spaced hair follicles that are distributed randomly over the surface of the scalp. Implanting generally involves instruments used by surgeons that are either designed to place hair grafts into pre-made wounds, or those that make wounds and implant hair grafts into the freshly made wounds.

One device for implanting FUs is seen in U.S. Pat. No. 5,951,572, which utilizes a plunger for urging an FU from within a cartridge into a body surface.

U.S. Pat. No. 6,585,746 discloses a hair transplantation system utilizing a robotic system, including a robotic arm and a hair follicle end effector associated with the robotic arm that could be used to harvest follicular units from the donor area and/or implant a hair follicle into the recipient area.

SUMMARY OF THE INVENTION

According to one aspect, a device is provided for implanting a follicular unit within a body surface while suppressing expulsion of one or more of adjacent implanted follicular units. In some embodiments the device comprises an implanting tool having a lumen sized to receive a follicular unit, a distal end of the tool having a tip for entering the body surface; and an anti-popping member operatively associated with the implanting tool. The anti-popping member generally extends radially outward from the implanting tool a distance sufficient to contact an area on the body surface adjacent the implanting tool (when the tip of the implanting tool enters the body surface) and suppress expulsion of one or more of adjacent implanted follicular units. The device may further comprise an outer elongated body (or tube or collar) having a throughbore, and wherein the implanting tool is mounted for translation along the throughbore of the outer elongated body. In some embodiments, the device includes means for expelling a follicular unit out of the lumen of the implanting tool, for example, an obturator. The anti-popping member may take various shapes and forms, including a convex shape on its distal side and a circular shape from a distal view, it may include a flange. It may be mounted, for example pivotally, on the outer tube. The anti-popping member may be adapted to be positioned, including by slidably moving, towards a distal end of the device for implanting. Furthermore, the anti-popping member may be configured so that at least a portion of the anti-popping member conforms to the body surface. The device for implanting according to various embodiments described herein may be incorporated into a robotic hair implantation system, or it may be incorporated into a handheld tool.

According to another embodiment, a device for implanting a follicular unit within a body surface while suppressing expulsion of an adjacent implanted follicular unit may comprise an implanting tool, for example, a needle or punch, having a lumen sized to receive a follicular unit, a housing to which the implanting tool is coupled for linear translation, and an anti-popping member associated with the housing and extending radially outward from the implanting tool. The anti-popping member may be coupled to move relative to the implanting tool in a second direction different from a direction of the linear translation of the implanting tool. The anti-popping member may pivot relative to the implanting needle, or it may be pivotally mounted to the housing. In some embodiments, the anti-popping member may be slidably moveable towards a distal end of the implanting tool. In some embodiments, the anti-popping member comprises a bearing surface, and the device includes a bearing arranged around the implanting needle on which the bearing surface of the anti-popping member pivots. The anti-popping member may further include a proximal shaft portion within which is defined at least a portion of the cavity, and the proximal shaft portion may further include at least one flexing section. One or more retainers may be positioned around the flexing section to help retain the anti-popping member on a bearing, such as a ball bearing.

According to still further embodiment, a system is provided for implanting a follicular unit within a body surface while suppressing expulsion of one or more adjacent implanted follicular units. The system comprises a membrane covering a portion of the body surface and through which an implanting tool, for example, a needle, passes before piercing the body surface, the membrane having sufficient contact with an area on the body surface adjacent the implanting needle to suppress expulsion of one or more adjacent implanted follicular units. In some embodiments, the membrane is elastic and self-seals the holes formed by through passage of the implanting needle. The system may include means for applying tension to the membrane; it may also include one or more fiducials for use as targets by an imaging system. In some embodiments, the system may comprise at least 2 membranes, a first membrane may be self-sealing and configured to be disposed adjacent to the body surface, and a second membrane configured to be disposed over the first membrane and be placed in tension. The above-mentioned fiducials may be positioned between the first and second membranes. The membrane(s) may comprise a liquid layer that solidifies after it is applied to the body surface. Anti-popping members, including membranes may be used in various systems, such as manual, partially or fully automated, including robotic systems.

Additionally, a method is provided for implanting follicular units within a body surface. The method comprising implanting one or more follicular units within a body surface while suppressing expulsion of at least one adjacent previously implanted follicular unit. Implanting and suppressing is accomplished using an anti-popping member operatively associated with an implanting tool. In various embodiments, the anti-popping member may comprise one or a plurality of membranes, and suppressing may comprise covering a portion of the body surface with the one or the plurality of anti-popping membranes through which the implanting tool passes before piercing the body surface. The membrane would have sufficient contact with an area on the body surface adjacent the implanting tool to suppress expulsion of an adjacent implanted follicular unit. In other embodiments of the method, the anti-popping member may extend radially outward from the implanting tool, and suppressing may comprise contacting an area on the body surface with at least a portion of the anti-popping member when inserting the implanting tool into the body surface.

BRIEF DESCRIPTION OF THE DRAWINGS

Features and advantages of the inventions described herein will become appreciated as the same become better understood with reference to the specification, claims, and appended drawings wherein:

DETAILED DESCRIPTION OF THE PREFERRED EMBODIMENTS

In the following Detailed Description, reference is made to the accompanying drawings, in which are shown by way of illustration specific embodiments in which the invention may be practiced. In this regard, directional terms, such as "top," "bottom," "front," "back," "distal," "proximal," etc., are used with reference to the orientation of the Figure(s) being described. Because components or embodiments can be positioned in a number of different orientations, the directional terminology is used for purposes of illustration and is in no way limiting. It is to be understood that other embodiments may be utilized and structural or logical changes may be made without departing from the scope of the inventions described. The following Detailed Description, therefore, is not to be taken in a limiting sense, and the scope of the invention is defined by the appended claims.

It should be understood that the representative devices and methods described herein are suited for use with a robotic system for hair implanting and transplanting. However, they are not limited by any means to the robotic applications; instead the described devices and methods may be applied to the procedures with various degrees of automation as well as to the manual procedures conducted, for example, by a human with a hand-held device. Such hand-held devices could be, for example, operably connected to the computer processor and imaging system. Therefore, manual, partially and fully automated systems are all within the scope of the invention.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated processes described herein may also be robotically-assisted or computer/software/machine-instruction controlled. The devices and methods of the present invention are useful in manual procedures and systems, as well as in automated procedures and system, and they are also useful in the robotically-assisted systems and procedures. In contrast, the adverb "automatically" when referred to use of a particular component of a system or a particular step in a process means that such step is accomplished autonomously, i.e., without real-time manual assistance.

The term "tool" as used in implanting tool with reference to a hair transplantation procedure refers to any number of tools or end effectors that are capable of implanting/inserting FUs into a body surface. Such tools may have many different forms and configurations. In some embodiments, the tool comprises a hollow tubular shaft. The distal end of implanting tools may be sharpened so as to perform puncture and delivery of the FU in one operation. Alternatively, the puncture may be formed by another tool, with the implanting tool being relatively blunt and used just for delivery of the FU. It also should be noted that harvesting and implanting tools could be the same or different instrument, depending on the procedure and objects to be removed or harvested. The terms "coupled," or "attached," or "connected," or "mounted" as used herein, means directly or indirectly coupled, attached, connected, integrated, or mounted, for example, through one or more intervening components.

Figure 1A:
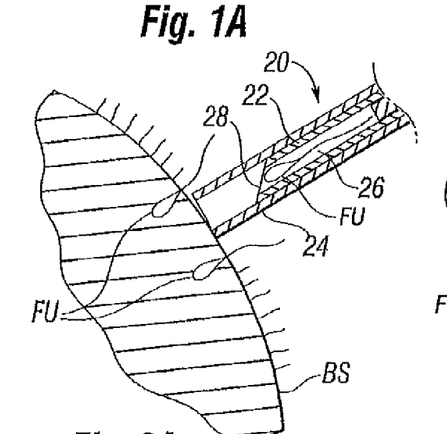
FIG. 1A is a sectional view of a portion of a body surface and a follicular unit (FU) implant device poised just above before implanting an FU.

FIG. 1A shows a portion of a body surface BS in cross section with a follicular unit (FU) implant device 20 disposed above the body surface BS prior to implanting an FU at a target location. The body surface BS may be a bald, thinned, or other such recipient area into which FUs will be implanted. Two previously implanted FUs are shown adjacent to the target implantation location. An illustrative implant device 20 includes an implant tool 22 arranged to reciprocate along the throughbore of an outer tube or elongated body 24. The implant tool 22 has a lumen 26 sized for receiving a FU and a sharp distal end 28 for piercing the body surface BS. The implant tool 22 may take a variety of forms, for example, a needle or a punch. Illustrative outside diameters of the implant tool 22 range between 0.5-1.5 mm.

Figure 1B:
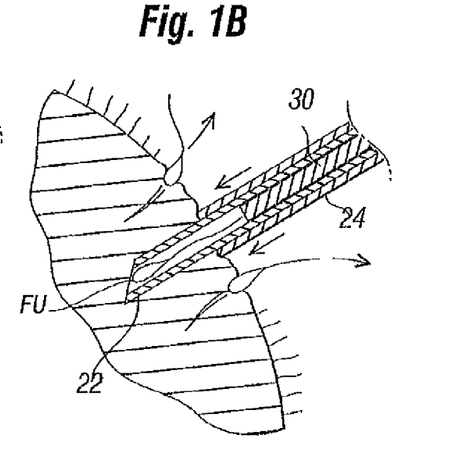
FIG. 1B is a sectional view of a portion of a body surface like FIG. 1A with the implant device in the process of implanting an FU, and showing potential expulsion of adjacent implanted FUs.

FIG. 1B illustrates the implant device 20 with an FU urged through the lumen 26 by an obturator 30 for implanting into body surface BS. FIG. 1B illustrates a problem occurring while the recipient site implantation is in progress, which is referred to as "popping" or dislodging of implanted follicular units. Because of downward pressure on the body surface BS by the implant device 20, adjacent previously-implanted FUs may be expelled or at least partially expelled as shown. That is, typically the outer tube 24 depresses the body surface BS prior to puncture of the skin or body surface with the implant tool 22. Compression of the tissue adjacent the target location propagates through the tissue and may extrude or expel the FUs that are located close by. Even if the previously implanted FUs are not completely expelled, they may be urged closer to the skin or body surface, thus compromising their successful transplant. Care by the operator can reduce the number of expelled or otherwise compromised FUs during the implant process, but inevitably some expulsion/compromising occurs which reduces the yield and increases the time for the entire process. "Popped" grafts may be manually replaced into their recipient sites when the displacement is noted. Downward pressure with a moist gauze pad placed over a site of previous implantations is a common aide to prevent popping during the procedure.

The present application is directed to providing a tool and method for improving efficiency of the implantation process, and in particular helping to reduce "popping" and improve retention of implanted follicular units within the body surface. Described herein are a number of "anti-popping" members for suppressing expulsion of FUs adjacent the FU being implanted. As will be explained below, the anti-popping members may be attached or mounted on the implant tool, integrated into the implant tool, or applied to the body surface BS prior to the implant procedure. These alternative structures, and others, enable a process for implanting follicular units within a body surface BS that utilizes an implant device or tool to implant the FUs while simultaneously suppressing expulsion of at least one adjacent, implanted, follicular unit.

Figure 2A:
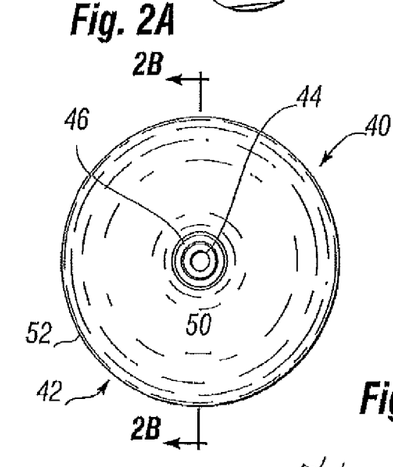
FIGS. 2A and 2B are end elevational and longitudinal sectional views of an exemplary follicular unit implant device having an anti-popping member disposed about a distal end.
Figure 2B:
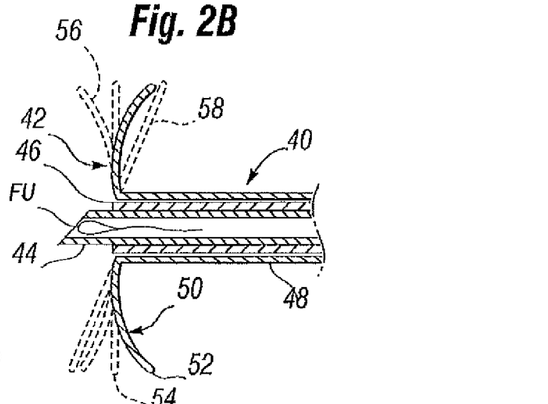

FIGS. 2A and 2B illustrate an example of a FU implant device 40 according to a first embodiment, having an anti-popping member 42 disposed about a distal end thereof. As with many known implant tools, the improved implant device 40 may comprise a sharp-tipped implant tool 44 having a lumen sized to receive an FU that linearly translates within the throughbore of an outer tube or collar 46 (the outer tube/elongated body or collar 46 is optional and may be omitted in some embodiments). Alternatively, the implant tool 44 may be relatively blunt-tipped and used to insert FUs within preformed openings. The anti-popping member 42 may include a proximal shaft portion 48 fitted around the collar 46 (if present) and a distal flange 50 that extends radially outward therefrom. The anti-popping member 42 is operatively associated with the implant tool 44. For example, the anti-popping member 42 may be mounted rigidly to the collar 46, or may be mounted to a housing, or proximal handle or collet (not shown) of the implant device 40. In general, when collar 46 is present, the anti-popping member 42 and collar 46 may move together, while the implant tool 44 may translate longitudinally with respect thereto, although there may also be relative movement between the anti-popping member and the collar. Alternatively, the anti-popping member may be incorporated into the implant tool, providing an integrated structure.

As seen in the configuration illustrated in FIG. 2B, the distal flange 50 of the anti-popping member 42 (shown in solid line) commences at an axial location that is just proximal to the distal end of the collar 46. The flange 50 projects radially outward a distance sufficient to apply a pressure footprint to the body surface BS surrounding or adjacent the collar 46 and prevent expulsion of adjacent, previously-implanted FUs. In one embodiment, the flange 50 is centered about the collar 46 and has a diameter of between about 0.5-1.5 inches, more preferably between about 0.5-1.0 inches. In another embodiment the flange 50 as viewed from the distal direction is circular, although oval, polygonal, or other shapes are possible. The flange can be made from various materials, including metal, plastic, and other materials. It can be flexible, or rigid.

In the illustrated embodiment, the flange 50 has an outer edge 52 that is relieved in a proximal direction relative to the central region of the flange. For example, the flange 50 may gradually curve in a proximal direction toward the outer edge 52, so as to be convex facing the body surface BS. Providing this shape helps the flange 50, or at least a portion of it, conform to uneven or angled body surfaces. Alternatively, the shape of flange may take a number of other configurations as illustrated by the dashed lines in FIG. 2B, though the shape is not limited to the configuration shown. In a first alternative, seen at 54, the flange 50 extends linearly radially outward from the collar 46. A concave-distal version of the flange 50 is seen at 56, while an angled version is shown at 58. With respect to the angled version 58, the flange may be journaled to rotate about the collar 46 (or the implant tool 44) such that the anti-popping member 42 can be oriented in a manner that best conforms to the particular body surface BS. Or, the user may simply rotate the entire device to better conform the angled flange 58.

Figure 3:
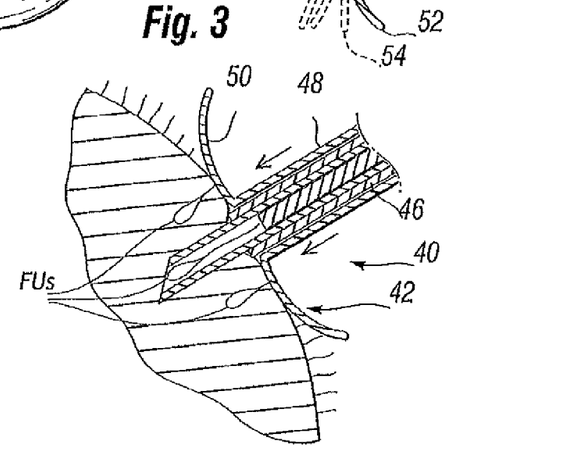
FIG. 3 is a sectional view of a portion of a body surface showing the implant device of FIG. 2B in the process of implanting an FU, showing the anti-popping member suppressing expulsion of adjacent implanted FUs.

FIG. 3 is a sectional view of a portion of a body surface BS showing the implant device 40 of FIG. 2B in the process of an implanting an FU. At least a portion of the flange 50 of the anti-popping member 42 contacts the body surface BS and suppresses expulsion of adjacent implanted FUs. In one embodiment, the flange 50, and perhaps the entire anti-popping member 42, is made of a resilient material such as a silicone elastomer so that it flexes in contact with the body surface BS. Alternatively, the flange 50 may be made of a more rigid material, such as Delrin. Still further, the flange may pivot or flex about the proximal shaft portion 48, or the entire anti-popping member 42 may be arranged to slide axially with respect to the collar 46 (if present), such as by being spring-biased in a distal direction. Those of skill in art will understand that there are numerous alternative configurations for the anti-popping member 42.

Figure 4:
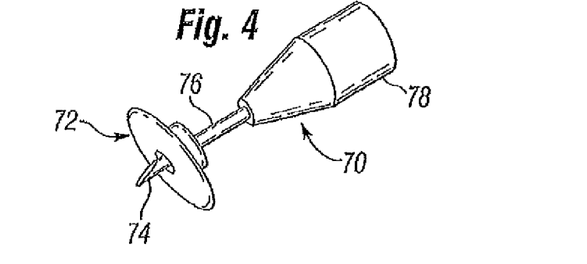
FIGS. 4, 5, and 5A are perspective, end elevational, and longitudinal sectional views of an alternative FU implant device having a pivoting anti-popping member.
Figure 5:
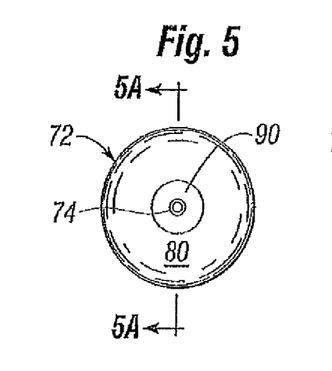
Figure 5A:
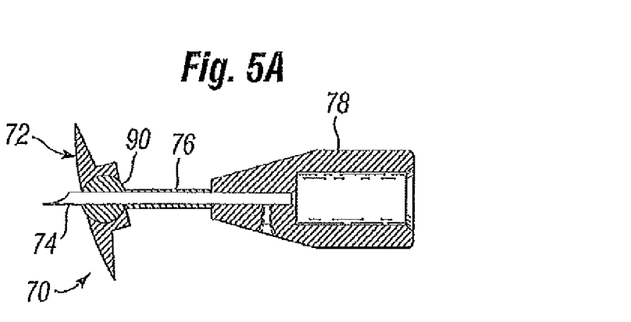

FIGS. 4, 5, and 5A illustrate an alternative FU implant device 70 having a pivoting anti-popping member 72. The implant device 70 includes, as before, the implant tool 74 having a lumen sized to receive follicular units (FUs). The tube or collar 76 in this embodiment is used as a "stop" to prevent a bearing 90 from pushing back or sliding up the implant tool or needle 74 during the implant process. The anti-popping member 72 pivots about the bearing 90. The collar 76 in turn, mounts within a distal end of a holding member, for example, a housing, or chuck or collet 78 of the implant device 70. The holding member or a collet 78 may be a component of a robotic hair transplantation system, such as that shown in co-pending U.S. patent application Ser. No. 12/194,370, filed Aug. 19, 2008, and expressly incorporated herein. In this regard, operation of the collet 78, the attached collar 76, and implant tool 74 may be controlled automatically or semi-automatically by a computer in conjunction with an imaging system (not shown). Alternatively, the collar 76 may form the distal tip of a hand-held or manual follicular unit implant device, such that operation of the respective components is done manually or with partial automation for each FU implanted.

Figure 6:
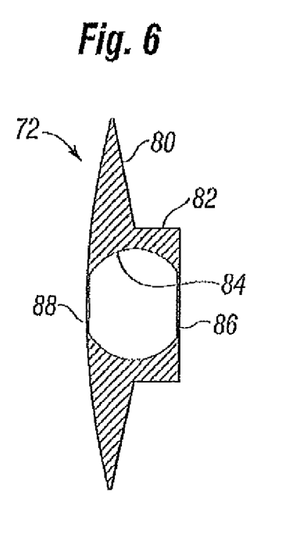
FIG. 6 is a sectional view of the pivoting anti-popping member of the alternative implant device of FIG. 5A.

In the illustrated embodiment, the anti-popping member 72, seen in cross-section in FIG. 6, has, for example, a lenticular or bi-convex flange 80 on the distal end of a shaft portion 82. A cavity 84 extends the longitudinal length of the anti-popping member 72. Both a proximal aperture 86 and a distal aperture 88 are defined at opposite ends of the cavity 84. The cavity 84 comprises a bearing surface to swivel over the exterior surface of a bearing 90 (shown in FIG. 5A) mounted at the distal end and around the implant tool 74. The proximal and distal apertures 86, 88 are smaller in diameter than the center of the cavity 84 and serve to retain the anti-popping member 72 on the bearing 90. In one embodiment, the pivoting anti-popping member 72 swivels about multiple axes.

In use, the alternative implant device 70 functions in a similar manner to the device 40 as illustrated in FIG. 3, with the implant tool 74 extending into a body surface to deposit a follicular unit FU. In this regard, a solid obturator such as that shown at 30 in FIG. 1B may be used to urge the FUs from the lumen of the implant tool 74, or periodic hydraulic or pneumatic pulses may be generated within the lumen to propel the FUs. The latter configuration is most effectively implemented using a robotic system, although a manual implant device may also be fitted with fluid pressure. The ventricular profile and swiveling nature of the anti-popping member 72 helps it conform to uneven body surfaces.

Figure 7:
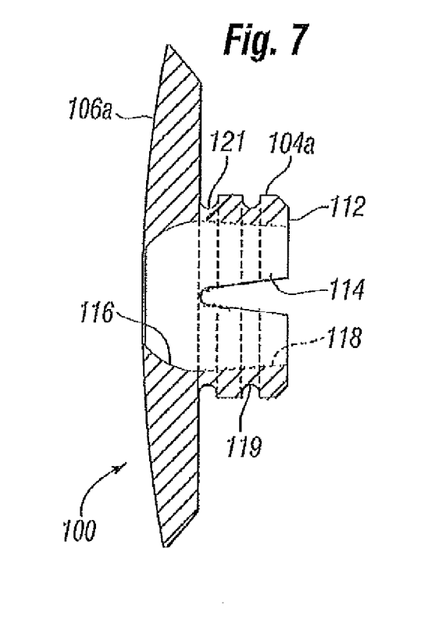
FIG. 7 is a sectional view of an alternative pivoting anti-popping member that could be used, for example, with the implant device of FIG. 5A.
Figures 8A, 8B, 9, 10, 11, 12:
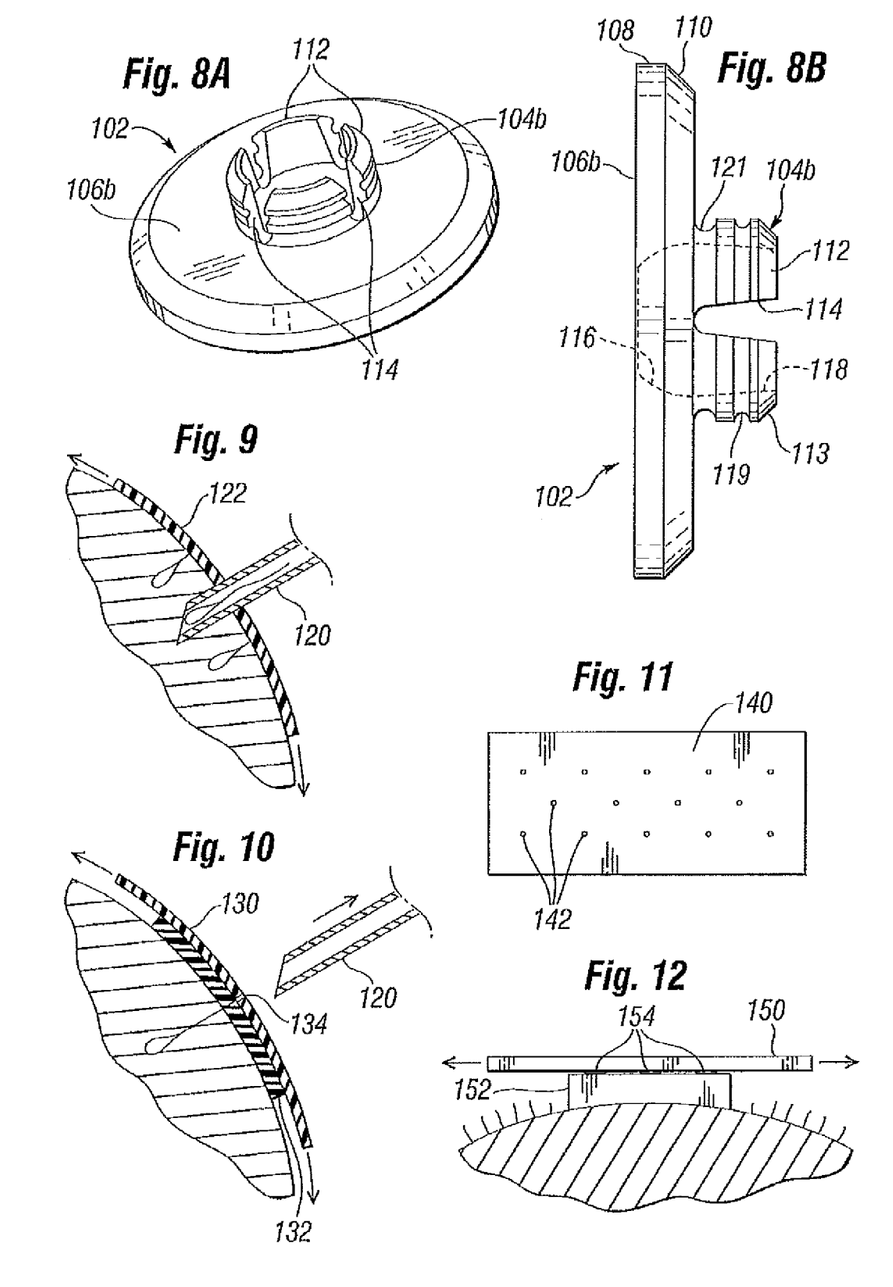
FIGS. 8A and 8B are perspective and side elevational view all of yet another alternative anti-popping member that pivots and could be used, for example, with the implant device of FIG. 5A.
FIG. 9 is a sectional view of a portion of a body surface showing an implant device in the process of implanting an FU through an anti-popping membrane.
FIG. 10 is a sectional view of a portion of a body surface showing an implant device just after implanting an FU through multiple anti-popping membranes.
FIG. 11 is a top plan view of an example of an anti-popping membrane having visual fiducials thereon for guiding the operator of the implant device.
FIG. 12 is a sectional view of a portion of a body surface showing first and second anti-popping membranes and visual fiducials sandwiched therebetween.

FIG. 7 illustrates an alternative pivoting anti-popping member 100, and FIGS. 8A and 8B show another pivoting anti-popping member 102, both of which could be used with the implant tool illustrated as an example in FIG. 5A. Both anti-popping members 100, 102 include a proximal shaft portion 104a, 104b and a distal outwardly-projecting flange 106a, 106b. The flange 106a in FIG. 7 has a convex distal face, while the flange 106b seen in FIG. 8B is flat. Furthermore, the flange 106b in FIG. 8B has an outer square shoulder 108 and a chamfer 110 that improves ease of manufacturing of the part. The proximal shaft portions 104a, 104b in these embodiments are both formed by a plurality of flexing sections 112 circumferentially disposed about a central throughbore and separated by, for example, V-shaped cutouts 114. Furthermore, both anti-popping members 100, 102 define bearing surfaces 116. As with the anti-popping member 72 of FIG. 4, the members 100, 102 swivel on a bearing, such as ball bearing, of an implant device. The circumferential flexing sections 112 may define therein a slightly tapered bore 118 that retains the members 100, 102 on their respective bearings, although tapering is not required. The flexing sections 112 thus facilitate assembly by permitting the members 100, 102 to be press-fit over the respective bearings. One or more retainers, such as retaining rings, (not shown) may be assembled in one or more grooves 119 defined on the exterior of the flexing sections 112. The proximal shaft portion 104b, as shown in FIG. 8B, may have a chamfer 113 that aids with the installation of the retaining ring(s). As seen in FIGS. 7 and 8B, anti-popping members may comprise a flexure undercut 121 that creates a flexure point and assists pivoting or otherwise conforming of the flange 106a or 106b to the body surface BS.

In addition to anti-popping members provided on the implant devices, anti-popping members may be applied to the body surface under treatment in order to suppress expulsion of previously-implanted FUs. In one such embodiment, the anti-popping members take the form of flexible membranes that conform to the affected body surface BS.

For example, FIG. 9 is a sectional view of a portion of a body surface BS showing an implant tool 120 in the process of implanting an FU through an anti-popping membrane 122. The membrane 122 preferably comprises a flexible material that self-heals as the implant tool 120 retracts from the body surface BS. For example, the membrane 122 may be a thin layer of polydimethylsiloxane (PDMS) stretched over the body surface. The thickness of the membrane 122 may, for example, be between 0.12-0.50 mm. Of course, those of skill in art will understand that various flexible materials and thicknesses may be substituted. Because the membrane 122 is stretched or tensioned, a barrier above the body surface BS is provided to minimize and preferably prevent expulsion of adjacent previously-implanted FUs.

FIG. 10 illustrates the implant tool 120 just after implanting an FU through multiply-layered anti-popping membranes 130, 132. To better retain the FU that is being implanted, a top layer membrane 130 is stretched over a bottom layer membrane 132 that is not in tension. Without the tension on the bottom layer membrane 132, it better seals the slit or hole formed by the implant tool 120 and prevents expulsion of the just-implanted FU. However, the top layer membrane 130 supplies a desirable tension and downward force on the bottom layer membrane 132 to help prevent expulsion of adjacent previously-implanted FUs. A small slit 134 in the top layer membrane 130 can be seen slightly expanded from the tension in the membrane. In one embodiment, the top layer membrane 130 is thinner than the bottom layer membrane 132. For example, the top layer membrane 130 may be between about 0.005-0.010 inches (0.127-0.254 mm), while the bottom layer membrane 132 may be between about 0.010-0.020 inches (0.254-0.508 mm). Both membranes 130, 132 may be formed of an elastomer, such as PDMS.

It should be understood that either the single layer membrane seen in FIG. 9, or the bottom layer of the dual-layer membrane seen in FIG. 10 may be applied to the body surface BS in liquid form and allowed to solidify by drying or other appropriate means, or at least partially solidify. Such a formed membrane may be removed after treatment, or subsequently when the patient washes the body surface.

In addition to providing the anti-popping function, the membranes described above may also supply fiducials for use as reference marks. The fiducials may be used for guiding the operator where to place the implant tool, or, for example, may be used with an imaging system for guiding a robotically-controlled implant tool. The fiducials may be visual, magnetic, or electronic, for example, or take any other appropriate form. For example, FIG. 11 is a top plan view of an exemplary anti-popping membrane 140 having visual fiducials 142 thereon. Such fiducials 142 can take the form of small dots or crosses which can easily be imaged under the naked eye, magnification or through a stereoscopic imaging system, for example. The fiducials 142 may be printed or embossed on the membrane 140, or may be applied to the membrane prior to use. The fiducials help the operator, or a computerized system, locate the appropriate point at which to implant the next FU.

FIG. 12 is a sectional view of a portion of a body surface showing first and second anti-popping membranes 150, 152 and visual fiducials 154 sandwiched therebetween, and may be detectable through the second (top) membrane. The fiducials 154 may be printed or embossed on either of the membranes 150, 152, or may be applied after first deploying the bottom layer membrane 152.

Furthermore, a method is provided for implanting follicular units within a body surface. The method comprising implanting one or more follicular units within a body surface while minimizing, or suppressing expulsion of at least one other adjacent previously implanted follicular unit. Implanting and suppressing may be accomplished substantially simultaneously using an anti-popping member operatively associated with an implanting tool. In various embodiments, the anti-popping member may comprise one or more membranes, and suppressing may comprise covering the body surface with the anti-popping membrane through which the implanting tool passes before piercing the body surface. The membrane would have sufficient contact with an area on the body surface adjacent the implanting tool to suppress expulsion of adjacent implanted follicular units. The membrane may be marked with fiducials. In other embodiments of the methods described herein, suppressing may comprise contacting an area on the body surface with at least a portion of the anti-popping member when inserting the implanting tool into the body surface, as seen for example in FIG. 3. The anti-popping member extending radially outward from the implanting tool, and may be positioned adjacent the distal end of the implanting tool.

While the preferred embodiments were described, it is to be understood that the words which have been used are words of description and not of limitation, and those skilled in the art will recognize that various modifications and improvements may be made to the invention without departing from the scope thereof. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. Therefore, changes may be made within the appended claims without departing from the true scope of the inventions described.

What is claimed is:

1. A method of implanting follicular units within a body surface, comprising:
   implanting one or more follicular units within a body surface while suppressing expulsion of previously implanted follicular units positioned adjacent and around a circumference of an implanting tool when a tip of the implanting tool enters the body surface,
   wherein suppressing is accomplished with a use of an anti-popping member configurable to extend radially outward from the implanting tool and covering an area substantially around the circumference of the implanting tool.

2. The method of claim 1, wherein the anti-popping member comprises a flange extending radially outward, and wherein suppressing comprises contacting an area on the body surface with at least a portion of the anti-popping member when inserting the implanting tool into the body surface.

3. The method of claim 1, wherein suppressing comprises conforming the anti-popping member to a portion of the body surface.

4. The method of claim 3, wherein conforming to the body surface comprises flexing the anti-popping member.

5. The method of claim 1, wherein suppressing comprises pivoting the anti-popping member relative to the implanting tool to suppress expulsion of the at least one of the adjacent previously implanted follicular units.

6. The method of claim 1, wherein implanting comprises expelling the one or more follicular units from a lumen of the implanting tool.

7. The method of claim 1, comprising moving the implanting tool in a linear translation direction and moving the anti-popping member at least in a second direction different from the direction of the linear translation of the implanting tool.

8. The method of claim 1, wherein suppressing comprises slidably moving the anti-popping member towards a distal end of the implanting tool.

9. The method of claim 1, wherein the method is performed using a robotic system.

10. The method of claim 1, wherein the anti-popping member comprises a bearing surface, the bearing surface arranged around the implanting tool, and suppressing comprises pivoting the bearing surface about the implanting tool.

11. The method of claim 1, wherein the anti-popping member comprises a flexure undercut, and the method comprising using the flexure undercut to assist in flexing the anti-popping member to conform to the body surface.

12. The method of claim 1, wherein the anti-popping member comprises fiducials or reference marks.

13. The method of claim 12, comprising using the fiducials or reference marks as a guide in placing the implanting tool.

14. The method of claim 1, wherein the anti-popping member comprises at least one anti-popping membrane and suppressing comprises covering a portion of the body surface with the at least one anti-popping membrane through which the implanting tool passes before piercing the body surface.

15. The method of claim 14, wherein covering the portion of the body surface comprises applying the anti-popping membrane in a liquid form, and allowing the liquid form to at least partially solidify.

16. The method of claim 15, wherein solidifying comprises drying.

17. The method of claim 14, wherein the anti-popping membrane comprises an elastic material and self-seals on retraction of the implanting from the anti-popping membrane.

18. The method of claim 1, wherein the anti-popping member comprises a multi-layered anti-popping membrane, wherein a first layer of the multi-layered anti-popping membrane is configured to suppress expulsion of the at least one previously implanted follicular unit, and further comprising suppressing the expulsion of a just-implanted follicular unit by use of a second layer of the multi-layered anti-popping membrane.

19. The method of claim 14, further comprising removing the at least one anti-popping membrane from the body surface.

20. The method of claim 8, further comprising preventing the anti-popping member from sliding up the implant tool during the implanting process.

21. The method of claim 1, wherein one or more steps of the method are computer-controlled.

22. The method of claim 1, comprising rotating the anti-popping member, a portion of the anti-popping member, or the anti-popping member together with the implanting tool to orient the anti-popping member for better conformance to the body surface.

* * * * *

UNITED STATES PATENT AND TRADEMARK OFFICE
CERTIFICATE OF CORRECTION

| | | |
|---|---|---|
| PATENT NO. | : 9,138,255 B2 | |
| APPLICATION NO. | : 13/545807 | |
| DATED | : September 22, 2015 | |
| INVENTOR(S) | : Clifford A. Oostman, Robert L. Weglinski and Timothy J. Kirkley | |

It is certified that error appears in the above-identified patent and that said Letters Patent is hereby corrected as shown below:

In the Claims

Column 10, line 1 (claim 5) - Delete the word "the" before "at least one of the adjacent".

Signed and Sealed this
Fifteenth Day of March, 2016

Michelle K. Lee
*Director of the United States Patent and Trademark Office*